(12) United States Patent
Streifinger et al.

(10) Patent No.: US 7,713,242 B2
(45) Date of Patent: May 11, 2010

(54) VALVE ARRANGEMENT FOR SURGICAL INSTRUMENTS AND VALVE CAGE FOR ACCOMMODATING THE VALVE ARRANGEMENT

(75) Inventors: Wolfgang Streifinger, Friedberg-Statzling (DE); Gerald Storm, Augsburg (DE)

(73) Assignee: Karl Storz GmbH & Co. KG (DE)

( * ) Notice: Subject to any disclaimer, the term of this patent is extended or adjusted under 35 U.S.C. 154(b) by 297 days.

(21) Appl. No.: 10/476,546

(22) Filed: Jun. 10, 2004

(65) Prior Publication Data
US 2005/0085774 A1 Apr. 21, 2005

(30) Foreign Application Priority Data
May 2, 2001 (DE) ................ 101 21 356

(51) Int. Cl.
*A61M 5/178* (2006.01)
(52) U.S. Cl. ............... 604/167.04; 604/167.02; 604/167.03
(58) Field of Classification Search ........... 604/167.01, 604/167.02, 167.03, 167.04, 167.05, 167.06, 604/30, 32–34
See application file for complete search history.

(56) References Cited

U.S. PATENT DOCUMENTS

| | | | | |
|---|---|---|---|---|
| 3,402,710 | A | 9/1968 | Paleschuck | 128/1 |
| 3,710,942 | A | 1/1973 | Rosenberg | 210/136 |
| 4,181,132 | A * | 1/1980 | Parks | 607/106 |
| 4,424,833 | A | 1/1984 | Spector et al. | 137/849 |
| 4,475,548 | A | 10/1984 | Muto | 128/207.14 |
| 4,634,424 | A | 1/1987 | O'Boyle | 604/51 |
| 5,207,656 | A * | 5/1993 | Kranys | 604/256 |
| 5,342,316 | A * | 8/1994 | Wallace | 604/256 |
| 5,356,381 | A | 10/1994 | Ensminger et al. | 604/93 |
| 5,360,417 | A | 11/1994 | Gravener et al. | 604/278 |
| 5,527,277 | A | 6/1996 | Ensminger et al. | 604/93 |
| 5,549,651 | A | 8/1996 | Lynn | 604/283 |
| 5,569,235 | A | 10/1996 | Ross et al. | 604/403 |

(Continued)

FOREIGN PATENT DOCUMENTS

DE 43 03 026 8/1994

(Continued)

OTHER PUBLICATIONS

German Search Report, Oct. 24, 2001, 4 pages.

(Continued)

*Primary Examiner*—Kevin C Sirmons
*Assistant Examiner*—Bhisma Mehta
(74) *Attorney, Agent, or Firm*—St. Onge Steward Johnston & Reens LLC

(57) ABSTRACT

The invention relates to a valve arrangement for surgical instruments, particularly trocars, such as those used for minimally invasive operations, e.g. operations involving laparoscopic techniques. The invention also relates to a valve cage for accommodating the valve arrangement. The valve arrangement comprises a valve body made of closed-cell, gas-tight foam material having at least one slot, which passes through the valve body and which is provided for introducing a surgical instrument guided inside the trocar. The valve cage is provided in the form of a housing whose shape and size are adapted to the outer dimensions of the valve body. The housing can be joined to a conventional trocar sleeve in a sealed and detachable manner.

17 Claims, 6 Drawing Sheets

U.S. PATENT DOCUMENTS

| | | | |
|---|---|---|---|
| 5,584,808 A | 12/1996 | Healy | 604/86 |
| 5,613,954 A * | 3/1997 | Nelson et al. | 604/167.03 |
| 5,782,817 A | 7/1998 | Franzel et al. | 604/256 |
| 5,873,862 A * | 2/1999 | Lopez | 604/249 |
| 5,931,801 A | 8/1999 | Burbank et al. | 604/4 |
| 6,146,362 A | 11/2000 | Turnbull et al. | 604/256 |
| 6,171,287 B1 * | 1/2001 | Lynn et al. | 604/256 |
| 6,221,056 B1 * | 4/2001 | Silverman | 604/167.02 |
| 6,254,529 B1 * | 7/2001 | Ouchi | 600/154 |
| 6,482,181 B1 * | 11/2002 | Racenet et al. | 604/167.06 |

FOREIGN PATENT DOCUMENTS

| | | |
|---|---|---|
| DE | 43 12 961 A1 | 10/1994 |
| DE | 296 19 635 | 2/1997 |
| DE | 196 19 065 | 11/1997 |
| DE | 694 13 644 | 4/1999 |
| DE | 697 00 124 | 6/1999 |
| DE | 199 25 324 | 1/2001 |
| EP | 0 283 060 | 2/1988 |
| GB | 2 275 420 | 8/1994 |
| WO | 95/32019 | 11/1995 |

OTHER PUBLICATIONS

International Search Report, Oct. 24, 2002, 6 pages.

* cited by examiner

VALVE ARRANGEMENT FOR SURGICAL INSTRUMENTS AND VALVE CAGE FOR ACCOMMODATING THE VALVE ARRANGEMENT

FIELD OF THE INVENTION

The present invention is concerned with a valve arrangement for surgical instruments, particularly trocars, such as those used for minimally invasive surgery, e.g., surgery involving laparoscopic techniques. Also described is a valve cage for accommodating the valve arrangement.

BACKGROUND OF THE INVENTION

The prior art in this context is reflected in the printed publications U.S. Pat. No. 5,207,656, U.S. Pat. No. 5,549,651, and U.S. Pat. No. 4,475,548, with U.S. Pat. No. 5,207,656 being the most closely related. It reveals a medical instrument valve having a foamed sealing region, for example in the form of a catheter introducer. The housing incorporates a valve for receiving and sealing an elongated member, which penetrates the valve. The valve itself incorporates an elastomeric partition member. This partition member is presented to facilitate the penetration and sealing of an elongated member into the body. It comprises a closed-cell foamed material, inside which a fluid is enclosed as a lubricant, to support the penetration by an elongated member by reducing the friction. It is a shortcoming of this embodiment that the outer surface of the foamed material, i.e., the side in which an elongated member is to be inserted into the valve, is designed flat. This can make it difficult to precisely position the elongated member for its penetration of the foamed material member. This means that at times a passage has to be found through the foamed material member. This is not pleasant, however, for the patient or for the medical personnel.

U.S. Pat. No. 5,549,651 describes a medical valve and fluid transfer method. The context is an intravenous tubing system that is provided with a valve. The valve has a piston and a seal affixed to its front for the tubing system. Only the seal is manufactured of an elastic material. It is positioned in a guide means disposed perpendicular to the main line. This guide means has, in the proximal region, in the longitudinal direction, viewed in the direction of the main line, two opposed projections that the seal squeezes together in these two regions when the seal is guided into this direction. The seal has a continuous slit along the length, which, during the insertion process, forms an oval opening through pressure onto the two laterally disposed pressure points. A fluid may now be passed through this opening. However, no provision is made for a supply with a medical instrument, as in the previously mentioned patent documents.

U.S. Pat. No. 4,475,548 describes a valve body. The foamed material of the valve body is preferably a surgical rubber material that has been foamed. According to its description it does not form any closed cells. For the patent document, this has the advantage that an exchange of fluid is possible from one cell to the next. However, at the same time this also means that a gas-tight implementation is not possible. An absolute seal between a space located behind a body cavity and the environment can thus not be created. It is thus not possible to perform surgery under sealed conditions.

Trocars are known both made of plastic as disposable articles, as well as made of metal as re-usable instruments, and essentially consist of a trocar sleeve, which is inserted into the abdominal wall, and a sealing arrangement in the form of a valve, which is disposed in a so-called valve cage in the form of a housing that is wider than the trocar sleeve and located at the access end of the trocar sleeve. The trocar sleeve and valve cage are generally connected to one another in a detachable manner to allow for easy cleaning.

Disposed inside the valve cage is a valve arrangement, which allows the inserted surgical instrument to pass through and provides a seal for the patient's abdominal cavity from the atmosphere when the instrument is removed, e.g., when instruments are changed. A rubber seal or rubber cap that has been adapted to the instrument diameter accomplishes the sealing of the abdominal cavity, after the instrument has been inserted.

Valve arrangements of this type require relatively large and heavy valve cages, which cause an undesirable "top-heaviness" of the trocar. Also, the conventional valves are difficult to clean and incomplete cleaning entails the risk of an infection to the patient.

SUMMARY OF THE INVENTION

It is the object of the invention to propose a valve arrangement and a suitable valve cage for trocars, which, in its sealing effect is comparable to the known valve arrangements, but which can be designed less expensively, smaller and with a lower weight, with the medical instruments being easier to insert.

This object is met with the characteristics of the independent claims.

In accordance with the invention, the valve body is composed of closed-cell, gas-tight foamed material having at least one slit penetrating the valve body for inserting surgical instruments that are guided inside the trocar.

The valve body is designed, e.g., as a rectangular or cylindrical block, which is delimited by an upper, a lower, and at least one lateral surface. It is important that the foamed material incorporates hollow spaces that are not in communication with one another, so-called vacuoles, and that it thus represents a gas-tight substance.

The surface that needs to be sealed is the inside valve slot. The tight fit for the instruments to be inserted is generated by the inherent elasticity of the foamed material; after removal of the instrument it automatically brings the sealing surfaces together, so that they are in sealing contact with one another. Due to the inherent elasticity of the foamed material, the valve surfaces that are created by the slit are pressed against one another (valve reset). When an overpressure is applied to the bottom side of the valve, the vacuoles react by lateral yielding, i.e., they are being compressed, causing them to press onto the valve surface. The finer (smaller) the vacuoles are featured, the more stable and stiffer the valve body.

If tissue enters into the slit, the valve nevertheless closes, as opposed to silicon flap valves, as it is softly enclosed by the foamed material and thus creates its own seal. The foamed material also serves to keep lubricating agents used to lubricate the instruments away from the abdominal cavity.

In one possible embodiment of the invention, the slit may be designed so long that it divides the valve member into two individual halves.

Two halves are easier to manufacture and introduce into the valve cage.

From a production point of view, these are then e.g., two separate blocks that are placed opposite one another in the valve housing. The wider the valve slit and the softer the valve material, the less pressure and, hence, friction, there is on the instrument moving inside; the flatter the valve (low construction height), the lower, again, the instrument friction.

In an improvement, provision is made for the upper surface of the valve body to be provided with a cutout that tapers substantially coniformly or cuneiformly towards the slit.

The surface of the cutout is preferably provided at least partly with a coating that is smooth and harder as compared to the foamed material and which may be composed of plastic, metallic, or ceramic material.

Due to the smooth coating of the cutout a certain sliding area and guide means is created for the instruments to be inserted so that instruments cannot puncture the foamed material member and the same is not damaged.

The coating may be substituted with a springy metal tongue, which is additionally turned down along its edges to prevent the instrument being inserted or removed from getting caught on the metal tongue.

In the region of the upper surface of the valve member an additional centering and guide sleeve may be provided to center and guide the instruments to be inserted. This sleeve also prevents possible damage to the foamed material member when the instruments are being inserted. If the foamed material member becomes damaged or torn, however, this does not necessarily mean that the valve has become leaky since the foamed material is inherently elastic and automatically returns to its original shape.

It is sufficient if the length of the centering sleeves is approximately 1.5 times the diameter of the instrument. The diameter does not need to be adapted overly precisely to the instrument diameter, instead the instrument only needs to be guided loosely inside it.

In a further embodiment the bottom surface of the valve body incorporates slanted pressure deflecting surfaces that extend in an acute to obtuse angle to the slit. This slanting on the over-pressure side, as it also exists in a similar form in the known flutter valve, deflects the pressure vector in such a way that the valve parts are pressed against one another.

A more pronounced closing effect can be obtained when the valve body is provided with at least one hollow space that laterally encompasses the slit at least partly, and which is open towards the bottom surface. One hollow space is preferably used per valve half.

The valve arrangements described herein can be used in combination with valve cages and trocar sleeves.

The valve arrangement is a disposable article and is disposed of together with the valve cage after it has been used and/or removed from the reusable valve cage.

The valve cage that is provided to accommodate the valve arrangement is a housing, preferably made of plastic, which is adapted in its shape and size to the outer dimensions of the trocar sleeve. The housing is connected to a conventional trocar sleeve in a sealing and detachable manner.

The valve cage with the valve arrangement is placed onto the multiple-use trocar, which has now been reduced to a simple tube, is used once, and then disposed of.

The valve cage is adapted to the standard instrument passage diameter, such as 2.5 mm, 5 mm, 10 mm, etc.

Compared to conventional valve cages, the inventive valve cage can be built significantly smaller and more light-weight due to the valve arrangement being of foamed material, since the valve opening radius is eliminated and the foamed material is very light-weight. Due to the porosity of the foamed material the massive silicon casting process can be bypassed, cutting down on mass and size.

As a result, the trocar no longer has a pronounced top-heaviness and does not constantly fall over onto the abdominal wall. Additionally, there is a gain in working height since the valve can be built slimmer, allowing the instrument to be pressed more flatly onto the abdomen, resulting in an enlargement of the action radius.

The one-time use of the valve cage results in reduced cleaning time and, hence, savings in labor time. A simplified cleaning of only the multiple-use trocar sleeve results in better hygiene and sterility.

The connection between the trocar sleeve and valve cage may be designed as a plug-type connection (clip), quarter-turn fastener, or screw-type connection. It is important that the connection between the trocar sleeve and valve cage is gas-tight.

The valve cage may incorporate, in a known manner, a connection for the gas supply, which is disposed below the valve body. However, the gas supply may also be disposed on the trocar sleeve.

Embodiments of the invention will be described below based on the figures in the drawing, which will also illustrate additional features, advantages and applications of the invention.

DETAILED DESCRIPTION OF THE INVENTION

Figure 1:
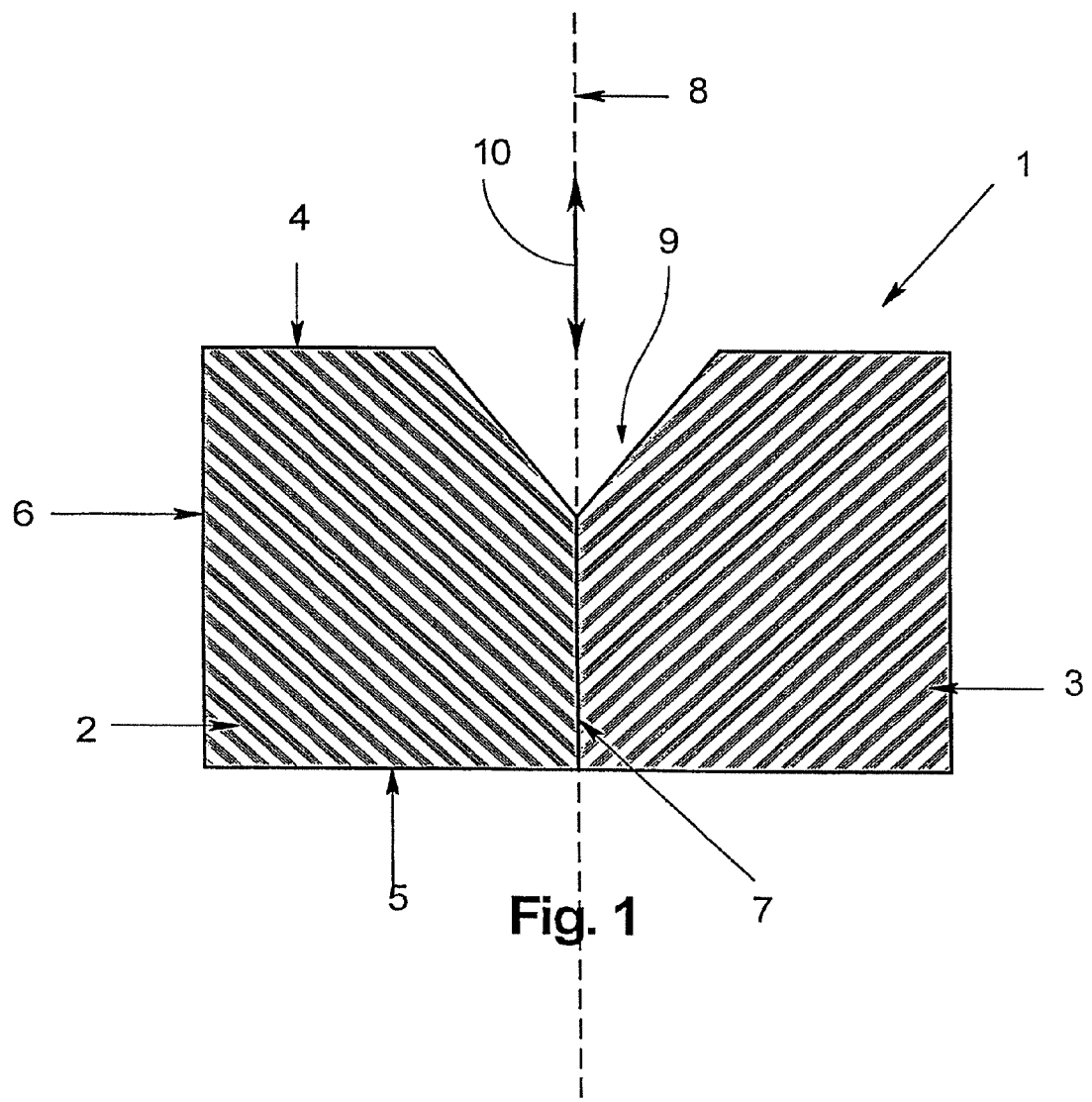
FIG. 1 shows a section through a first embodiment of the foamed material valve.

FIG. 1 shows a first embodiment of the inventive valve arrangement 1. The valve comprises a valve body 1 of closed-cell, gas-tight foamed material, which incorporates a slit 7 penetrating the valve body for inserting a surgical instrument that is guided inside the trocar. The slit extends vertically in the drawing along a valve plane 8 and divides the valve body 1 into a left body half 2 and right body half 3. The slit 7 may be designed such that the two body halves 2, 3 are connected to one another, however, it may also be designed such that the two body halves 2, 3 form separate foamed material bodies.

The upper surface 4 of the valve body 1 has a cutout 9 that tapers substantially cuneiformly or coniformly towards the slit to facilitate the insertion of a surgical instrument in the downward direction of the arrow 10. The side surfaces 6 and bottom surface 5 are adapted to a valve cage for accommodating the valve arrangement. The valve cage will be described below.

Figure 2:
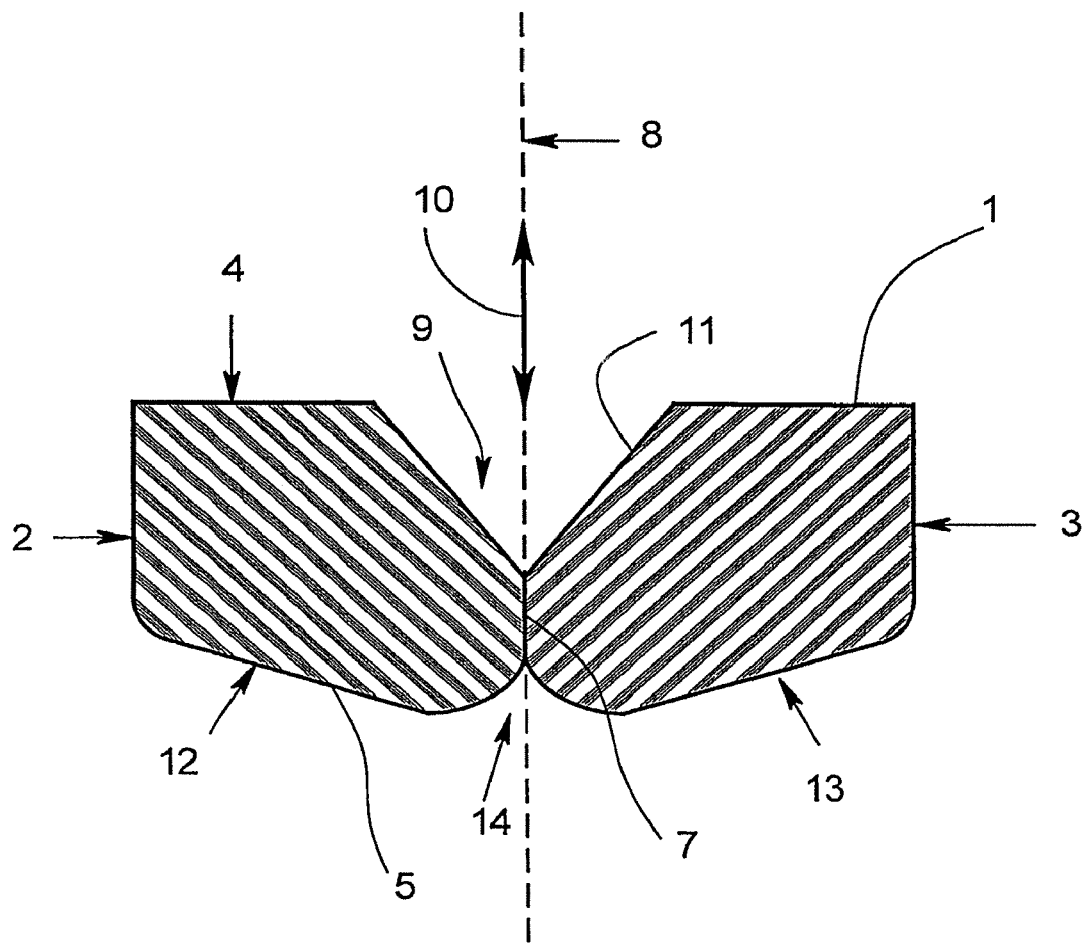
FIG. 2 shows a section through an additional embodiment of the foamed material valve.

An embodiment of the valve arrangement that is modified from FIG. 1 is shown in FIG. 2. In contrast to FIG. 1, the cutout 9 is provided in the upper surface 4 of the valve body with a smooth coating 11 which may consist, e.g., of Teflon. This coating is intended to prevent the valve body 1 from becoming damaged when a surgical instrument is inserted in the downward direction of the arrow 10. The coating 11 simultaneously also serves as a guide means for the instrument in the direction of the valve slit 7.

The underside 5 of the valve body, starting from the slit 7, is provided with slanted pressure deflecting surfaces 12, 13. During surgery the bottom surface 5 of the valve body 1 is subject to overpressure, which acts upon the pressure deflecting surfaces 12, 13 and presses together the body halves 2, 3 in the region of the slit.

Just as on the upper surface 4, the bottom surface 5 may also be provided with a cutout 14 in the region of the slit 7 to permit removal of a surgical instrument without damage to the foamed material member 1.

Figure 3:
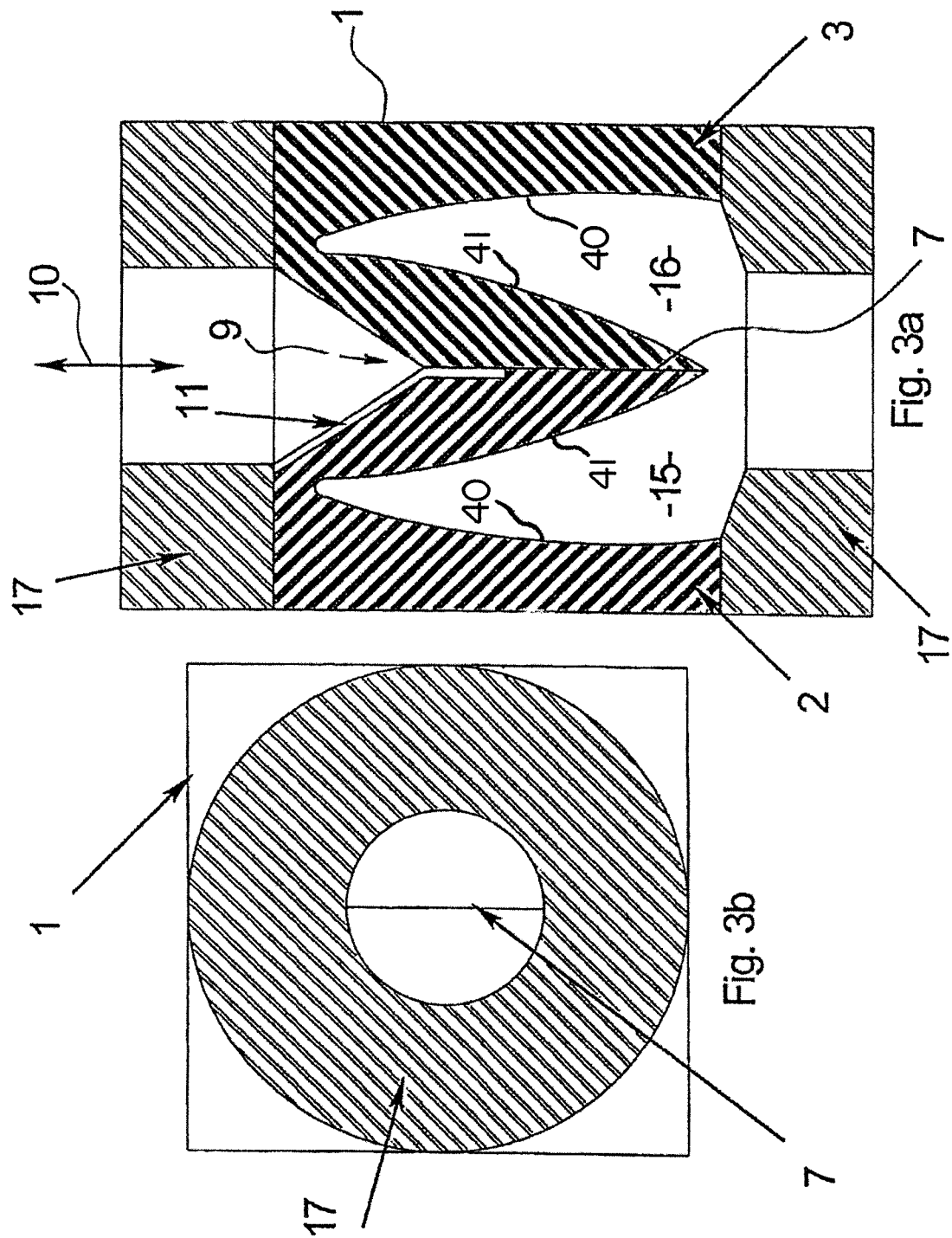
FIG. 3*a* shows a section through a third embodiment of the foamed material valve.
FIG. 3*b* shows a top view of FIG. 3*a*.

FIGS. 3*a* and 3*b* show a widened valve arrangement with a valve body 1 consisting of two body halves 2, 3, which are partly separated by the slit 7. In this embodiment a part of the upper surface of the valve body formed by the cutout 9 is provided only on one side with a coating 11, which partly extends even into the slit 7. This is intended to achieve an even better guiding of the inserted surgical instrument. The upper surface of the valve body comprises a beveled taper towards the plane of the slit to facilitate the insertion of a surgical instrument in the downward direction of the arrow 10 when the surgical instrument is received at the upper surface prior to inserting the surgical instrument.

Above and below the valve body 1, normal rubber seals or lubricating seals 17 are provided, which come to rest against the outer circumference of an inserted surgical instrument, sealing same in its inserted condition and, depending on the embodiment, providing additional lubrication to same.

Each body half 2, 3 has a hollow space 15, 16, which is open towards the bottom. FIGS. 3*a* and 3*b* show that hollow spaces 15, 16 form a ring shaped hollow space with an outer circumference 40 and an inner circumference 41 that encompasses a portion of the valve body penetrated by the slit prior to the insertion of a surgical instrument, are disposed beneath the portion of the valve body comprising the beveled cutout, and circumferentially surround a portion of the beveled cutout. The outer circumference 40 of the ring shaped hollow space is formed by valve body 1. A portion of the valve body penetrated by the slit extends into hollow space 15, 16 towards the bottom surface prior to insertion of the instrument. FIG. 3*a* also depicts that this portion can be formed by slanting surfaces of the valve body that cause the width of the portion of the valve body encompassed by the hollow space 15, 16 to narrow in the direction of the bottom surface. The hollow spaces 15, 16 are under pressure during surgery and guide the pressure vector, particularly towards the valve slit 7. The body halves 2, 3, are thus additionally pressed together in the region of the slit 7, so that a particularly good sealing effect can be attained.

In FIG. 3*b* it is particularly apparent that the slit 7 is preferably provided only in the middle region of the valve body 1, so that the two body halves 2,3 are connected to one another in the remaining region.

Figure 4:
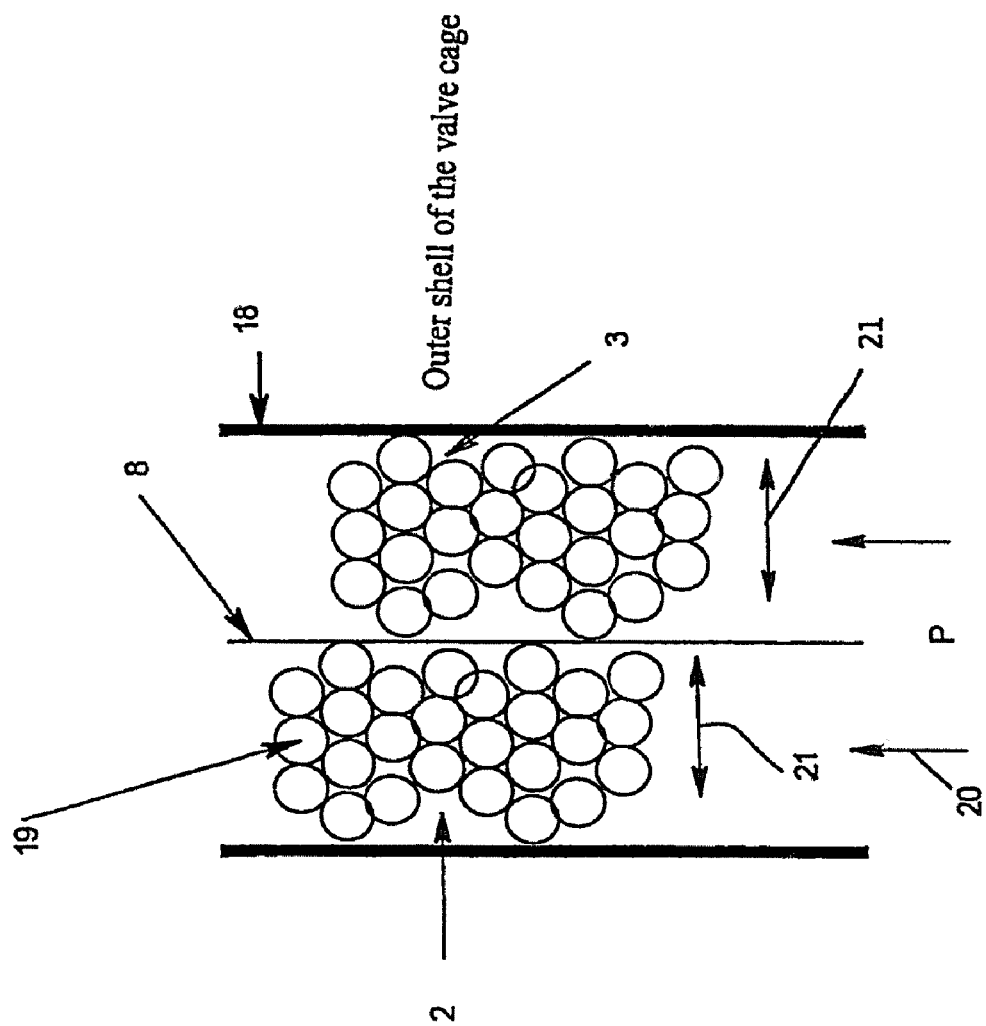
FIG. 4 shows a schematic presentation of the principle of operation of the foamed material valve.

FIG. 4 schematically shows the principle of operation of the inventive valve with a depiction of the two valve body halves 2,3, which consist of closed-cell foamed material, which incorporates a multitude of vacuoles 19. The valve body is disposed in a valve cage 18 and is laterally enclosed by same. If one side of the valve arrangement is now subject to overpressure, as indicated by the arrow 20, the vacuoles 19 are compressed and expand laterally in the direction of the arrow 21. This causes the body halves 2, 3 to be pressed on one hand against the wall of the valve cage 18 and on the other hand, to also be pressed together in the region of the valve plane 8, so that an excellent seal exists between the pressure side and surrounding atmosphere.

Figure 5:
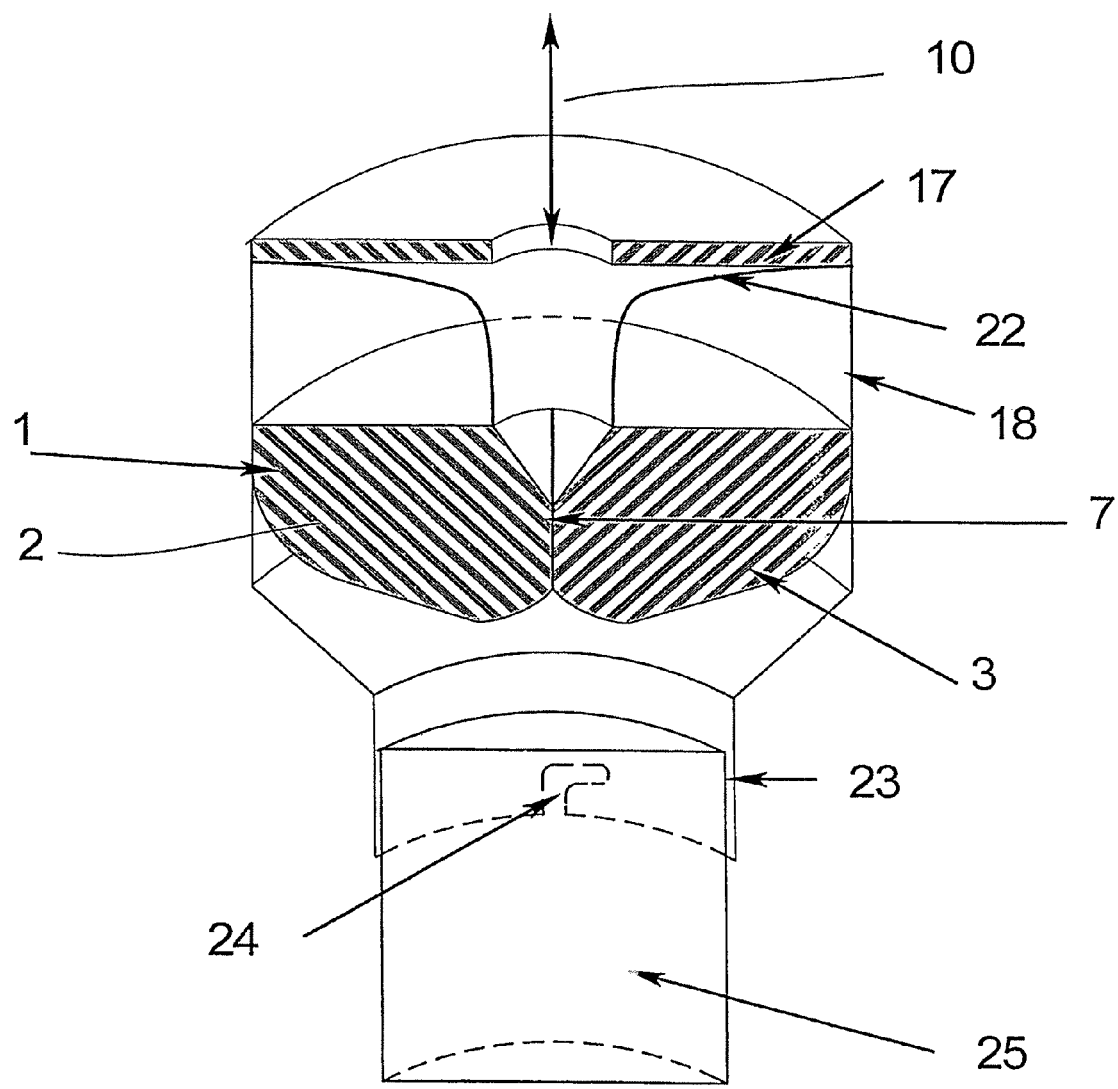
FIG. 5 shows a section through a valve cage with a valve arrangement.

FIG. 5 shows the valve cage 18, which incorporates a projection 23 and may be connected to a trocar sleeve 25. The connection may be made, e.g., with a quarter-turn fastener 24. Inside the valve cage the above-described valve arrangement is disposed in the two body halves 2, 3. Above the valve cage 1, a guide sleeve 22 may be provided to guide a surgical instrument being inserted in the downward direction of the arrow 10. Additionally, a rubber seal or lubricating seal 17 may be disposed above the guide sleeve 22, which has been described in connection with FIG. 3.

A valve cage of this type may have relatively small dimensions and, due to the valve arrangement consisting of foamed material, is also very light-weight. The valve cage 18 preferably consists of plastic.

Figure 6:
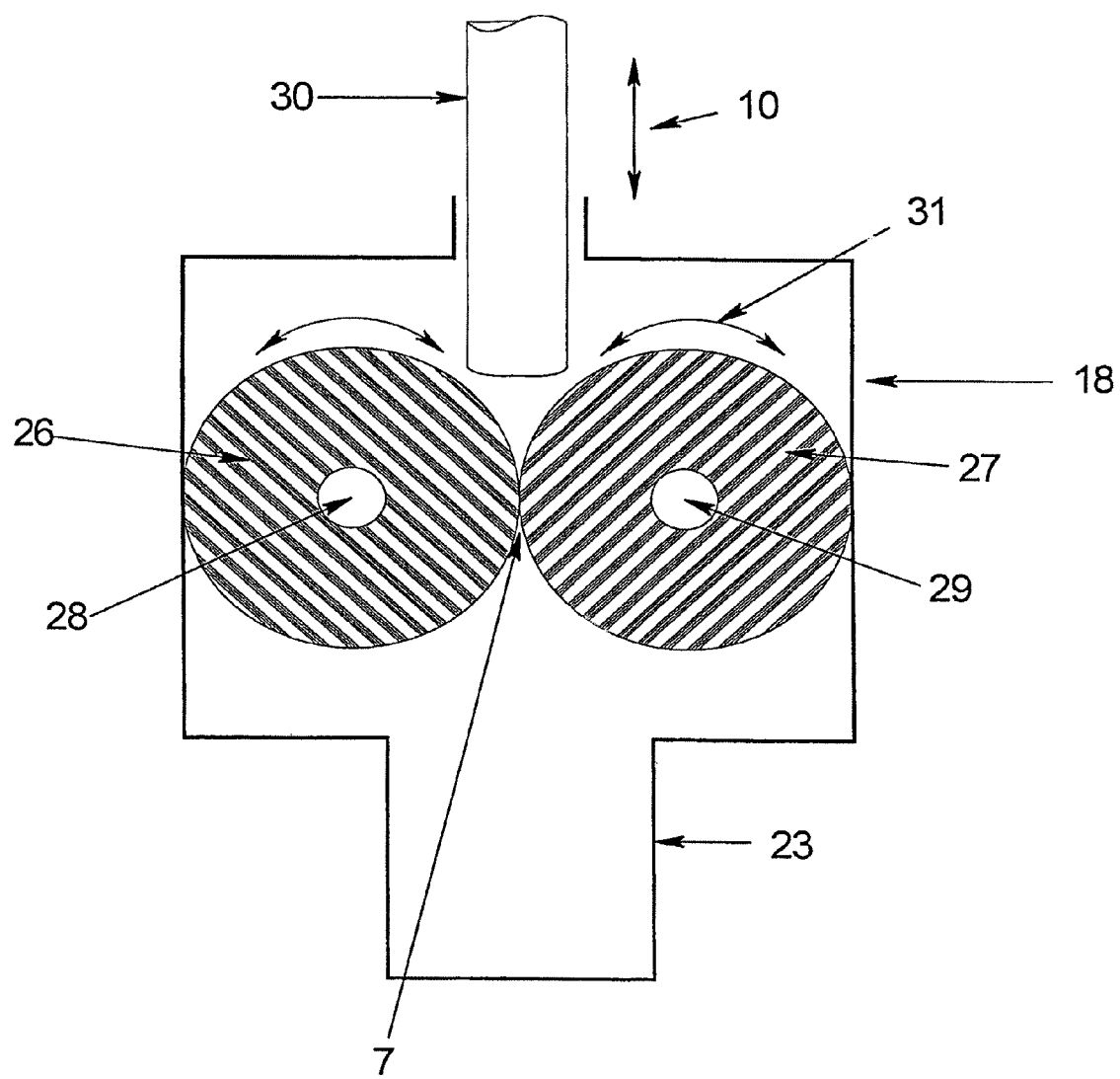
FIG. 6 shows a section through a valve cage with a valve arrangement in roller shape.

FIG. 6 shows a modified example embodiment of a valve arrangement disposed in a valve cage 18. The valve body 1, in this embodiment, comprises two foamed material rollers 26, 27, each of which is supported in a manner so that it can rotate about an axis 28, 29. The axes 28, 29 extend parallel to one another. The valve slit 7 is formed by the contacting surface of the two rollers 26, 27, which are movable against one another in the direction of the arrow 31. If a surgical instrument 30 is now inserted in the direction of the arrow 10, the rollers 26, 27 roll off on the surface of the instrument 30 and, through the inherent elasticity of the foamed material, ensure an excellent seal. On the other hand, the foamed rollers 26, 27 rest against the side wall of the valve body 18, so that a good seal is attained here as well. The foamed rollers 26, 27 are also composed of the closed-cell foamed material described above.

DRAWING LEGEND

1 Valve Body
2 Body Half
3 Body Half
4 Upper Surface
5 Bottom Surface
6 Lateral Surface
7 Slit
8 Valve Plane
9 Cutout
10 Direction of Arrow
11 Coating
12 Pressure Deflecting Surface
13 Pressure Deflecting Surface
14 Cutout
15 Hollow Space
16 Hollow Space
17 Lubricating Seal
18 Valve Cage
19 Vacuoles
20 Direction of Arrow
21 Direction of Arrow
22 Guide Sleeve
23 Projection
24 Quarter-Turn Fastener
25 Trocar Sleeve (Trocar Shaft)
26 Foamed Material Roller
27 Foamed Material Roller
28 Axis
29 Axis
30 Instrument
31 Direction of Arrow

What is claimed is:

1. A trocar comprising a trocar sleeve with a valve cage coupled to an access end of the trocar sleeve; wherein the valve cage comprises a valve arrangement for surgical instruments disposed inside the valve cage that allows an inserted surgical instrument to pass through, the valve arrangement having a valve body of closed-cell, gas-tight foamed material with an upper surface and a bottom surface, the valve body further incorporating at least one slit lying in a plane and penetrating the valve body for inserting a surgical instrument, wherein the valve body receives the surgical instrument at the upper surface prior to inserting the surgical instrument and the surgical instrument passes through the bottom surface when the surgical instrument is inserted, characterized in that the upper surface of the valve body incorporates a beveled cutout that tapers towards the plane of the slit and guides the surgical instrument towards the slit for inserting the surgical instrument;

wherein the valve body has a ring shaped hollow space with an outer circumference and an inner circumference, wherein the ring shaped hollow space is disposed beneath the portion of the valve body comprising the beveled cutout and above the bottom surface, wherein the outer circumference of the ring shaped hollow space is formed by the valve body, wherein a portion of the slit is surrounded by the ring shaped hollow space and extends into the ring shaped hollow space in the direction of the bottom surface prior to the insertion of the surgical instrument, wherein a portion of the beveled cutout is circumferentially surrounded by the ring shaped hollow space.

2. The trocar according to claim 1, characterized in that the valve body is designed as a block.

3. The trocar according to claim 1, characterized in that the slit divides the valve body into two halves.

4. The trocar according to claim 1, characterized in that the valve arrangement incorporates a centering and guide sleeve disposed in the region of the upper surface of the valve body for the instrument to be inserted.

5. The trocar according claim 1, characterized in that the valve arrangement is implemented as a disposable article.

6. The trocar according to claim 1, where the valve cage is characterized by a housing adapted in its shape and size to the outer dimensions of the valve body, which can be sealingly and detachably connected to the trocar sleeve.

7. The trocar according to claim 6, characterized in that the connection of the valve cage is implemented as a plug-type connection, quarter-turn fastener, or screw-type connection.

8. The trocar according to claim 6, characterized in that the valve cage rates a connector for the gas supply, which is disposed below the valve body.

9. The trocar according to claim 6, characterized in that the valve cage is composed of plastic.

10. The trocar according to claim 6, characterized in that the valve cage is implemented as a disposable article.

11. The trocar according to claim 1, characterized in that a surface of the cutout is provided at least partly with a protective coating.

12. The trocar according to claim 11, wherein the protective coating is a smooth and harder coating compared to the valve body.

13. The trocar according to claim 12, characterized in that the coating is composed of plastic, metallic, or ceramic material.

14. The trocar according to claim 1, wherein a portion of the valve body extends into the ring shaped hollow space in the direction of the bottom surface and includes at least one slanting surface.

15. The trocar according to claim 14, wherein the at least one slanting surface includes two slanting surfaces that are oriented such that the width of the portion of the valve body extending into the ring shaped hollow space in the direction of the bottom surface narrows in the direction of the bottom surface.

16. A valve arrangement for surgical instruments, having a valve body of closed-cell, gas-tight foamed material with an upper surface and a bottom surface, the valve body further incorporating at least one slit lying in a plane and penetrating the valve body for inserting a surgical instrument, wherein the valve body receives the surgical instrument at the upper surface prior to inserting the surgical instrument and the surgical instrument passes through the bottom surface when the surgical instrument is inserted, characterized in that the upper surface of the valve body incorporates a beveled cutout that tapers towards the plane of the slit and guides the surgical instrument towards the slit for inserting the surgical instrument;

wherein the valve body has a ring shaped hollow space with an outer circumference and an inner circumference, wherein the ring shaped hollow space is disposed beneath the portion of the valve body comprising the beveled cutout and above the bottom surface, wherein the outer circumference of the ring shaped hollow space is formed by the valve body, wherein a portion of the slit is surrounded by the ring shaped hollow space and extends into the ring shaped hollow space in the direction of the bottom surface prior to the insertion of the surgical instrument, wherein a portion of the beveled cutout is circumferentially surrounded by the ring shaped hollow space;

wherein a surface of the cutout is provided at least partly with a protective coating that is a smooth and harder coating compared to the valve body.

17. A valve arrangement for surgical instruments, having a valve body of closed-cell, gas-tight foamed material with an upper surface and a bottom surface, the valve body further incorporating at least one slit lying in a plane and penetrating the valve body for inserting a surgical instrument, wherein the valve body receives the surgical instrument at the upper surface prior to inserting the surgical instrument and the surgical instrument passes through the bottom surface when the surgical instrument is inserted, characterized in that the upper surface of the valve body incorporates a beveled cutout that tapers towards the plane of the slit and guides the surgical instrument towards the slit for inserting the surgical instrument;

wherein the valve body has a ring shaped hollow space with an outer circumference and an inner circumference, wherein the ring shaped hollow space is disposed beneath the portion of the valve body comprising the beveled cutout and above the bottom surface, wherein the outer circumference of the ring shaped hollow space is formed by the valve body, wherein a portion of the slit is surrounded by the ring shaped hollow space and extends into the ring shaped hollow space in the direction of the bottom surface prior to the insertion of the surgical instrument, wherein a portion of the beveled cutout is circumferentially surrounded by the ring shaped hollow space.

\* \* \* \* \*